(12) United States Patent
Bahk

(10) Patent No.: US 7,033,350 B2
(45) Date of Patent: Apr. 25, 2006

(54) HIGH POWER SEMICONDUCTOR LASER DIODE

(76) Inventor: Jong-Yoon Bahk, 38-504, Shinbanpo-3jigu apt., 1-1, Banpo2-dong, Seocho-gu, Seoul (KR) 137-042

( * ) Notice: Subject to any disclaimer, the term of this patent is extended or adjusted under 35 U.S.C. 154(b) by 313 days.

(21) Appl. No.: 10/332,396

(22) PCT Filed: Jul. 4, 2001

(86) PCT No.: PCT/KR01/01144

§ 371 (c)(1),
(2), (4) Date: Jul. 31, 2003

(87) PCT Pub. No.: WO02/03877

PCT Pub. Date: Jan. 17, 2002

(65) Prior Publication Data

US 2004/0215176 A1    Oct. 28, 2004

(30) Foreign Application Priority Data

Jul. 7, 2000    (KR) .................. 2000-0019541 U

(51) Int. Cl.
*A61B 18/18* (2006.01)
(52) U.S. Cl. .................. 606/12; 606/10; 606/11
(58) Field of Classification Search ........... 606/10–12
See application file for complete search history.

(56) References Cited

U.S. PATENT DOCUMENTS

| | | | | |
|---|---|---|---|---|
| 5,947,957 A | * | 9/1999 | Morris | 606/13 |
| 6,733,493 B1 | * | 5/2004 | Gruzdev et al. | 606/9 |
| 6,758,845 B1 | * | 7/2004 | Weckwerth et al. | 606/9 |
| 6,955,672 B1 | * | 10/2005 | Cense et al. | 606/9 |

* cited by examiner

*Primary Examiner*—A. Farah
(74) *Attorney, Agent, or Firm*—Lathrop & Gage LC

(57) ABSTRACT

The present invention relates to a portable laser treatment device, comprising case (10), semiconductor laser diode (11) which is installed inside the case (10) and irradiates laser, condensing lens (12) which is installed in front of the semiconductor laser diode (11), power supply, power switch (30) which is installed outside the case (10) and controls the supply of power, irradiation switch (31) which controls the irradiation of laser and controller (32) which controls the operation of the device according to the state of to switches, wherein distance detecting sensor (40) is installed on the case (10) to measure the distance between an irradiated surface and condensing lens (12) and said controller (32) receives signal from the distance detecting sensor (40) and cuts off laser irradiation when the distance between the irradiated surface and condensing lens (12) is greater than focal distance of the condensing lens (12).

4 Claims, 2 Drawing Sheets

HIGH POWER SEMICONDUCTOR LASER DIODE

TECHNICAL FIELD

The present invention relates to a portable medical laser treatment device, or more particularly to a portable laser treatment device, which uses a distance-sensing sensor and a thermal electric cooler.

BACKGROUND OF THE INVENTION

Generally, a laser beam has two important characteristics, i.e., spatial and wavelength coherency. Spatial coherency is a phenomenon of a laser beam traveling in a straight line without scattering, which results in gathering of laser beam while traveling far distance to the final target point with its size still similarly intact as compared to that of the laser beam originating from the light source. Wavelength coherency is a characteristic of constant wavelength of a laser beam so emitted.

The objectives of using laser devices in the field of medicine are based on a variety of academical and technical theories. Devices are widely used in various fields, such as incision of skin during surgery, coagulation of hemorrhage sites, tissue welding during anastomosis of tissues such as nerves and blood vessels, tissue vaporization, photodynamic diagnosis and treatment, resurfacing, revasculariziation, hair removal, and removal of artificial pigments. Also, a laser of certain wavelength is known to facilitate certain types of post-operation treatments.

Medical laser treatment devices have many advantages (infra) over electric cauteries or electric scalpels which have been used in surgeries and other treatments.

First, a laser beam, as its name suggests, is a light beam, not electricity. When a bodily stimulation is transmitted through nerves, it is transmitted as a minute electrical signal. Even if there were nerves present at the vicinity tissues adjacent to the target tissue under surgery, the laser unlike the electric scalpel does not affect the signal transmission of the nerves at all, and therefore its use therein results in prevention of unexpected nerve damage.

Second, there are many advantages of bloodless surgery. Upon irradiation of a laser beam thereto, the tissue incision along with small blood vessels are sealed. As such, by operating with laser scalpels, surgeries can be performed almost without hemorrhaging in cases of surgeries of organs with anticipation of much hemorrhaging, such as surgeries of patients with hemorrhage tendencies, or surgeries of organs with blood vessels, such as livers or kidneys. In this manner, the underlying conditions requiring blood transfusion to a patient vanishes, and in the end, bloodless surgery has the effect of preventing diseases, which can be disseminated by way of blood transfusion, such as hepatitis.

Third, small lymphatic vessels in tissues are sealed by means of irradiation of laser beams. As such, it sharply reduces the occurrence of edema caused by accumulation of lymph after surgery and also prevents spreading of cancerous cells during surgery or thereafter.

Fourth, as compared to surgeries using conventional surgical instruments, the surgeries using laser beams result in smaller post-surgery scars on patients. As such, the occurrence of one of the causes of re-surgery, a post-surgery stricture, can be effectively reduced.

Fifth, when surgery is performed by using a laser beam, it can effectively reduce post-surgery pain by sealing the nerve ends cut at the target site.

Sixth, the use of a laser beam leads to rapid recovery of a patient by facilitating the wound healing process after surgery.

Seventh, by using a laser, with the irradiation of the laser beam, it sharply reduces hemorrhaging by way of its hemostatic action. By reducing the time required for hemostatis to this extent, it effectively reduces the operation time therein.

Eighth, since the laser beam basically uses heat, the germs are destroyed at the treatment site even if there were a bit of infection at the treatment site. As such, it sharply decreases the occurrence of post-surgery infection.

Ninth, in the past, due to general anesthesia, patients had to be hospitalized for surgeries. However, by using a laser, which enables surgeries with local anesthesia, it has the effect of saving patient's time and treatment cost.

With all these advantages, however, the laser treatment devices are problematically large in volume and also expensive. Nonetheless, with the development of laser treatment devices of reduced volume, which use semiconductor laser diodes, their usage in medicine are gradually increasing.

However, a laser beam still has the characteristic of coherency. In other words, it has the characteristic of emitting a large amount of energy with no loss while traveling in a straight line without diffusion of laser beam of a given wavelength. Accordingly, if it is a laser beam, which has enough energy to incise a tissue, it can cause substantial damage upon reaching an undesirable site, which is outside the focus, due to some errors in the laser beam. In other words, since a portion of laser beam can be reflected, and the surface of the body, not within the objective under treatment, can be wrongfully irradiated on, which can cause substantial damage if irradiated onto the body with almost no loss of its harmful energy. Due to this type harm, due caution is required while operating a medical surgery laser. For this purpose, the operation switch is duplicated in installation to prevent careless manipulation. Nonetheless, such precautious measures are insufficient in view of the capacity of the operators and the fact the object of harm is after all a human body.

Further, the semiconductor laser diode, which corresponds to a laser oscillator device, gives off too much heat due to its operational conditions. As such, it needs some means of cooling In the past, devices using water-cooling or air-cooling means were used. If theses types of water-cooling or air-cooling devices were installed thereto, there would be a limitation against reducing the overall size of a laser treatment device. Consequently, there were thorny problems with respect to difficulties in usage and handling due to its general increase in weight.

SUMMARY OF THE INVENTION

In resolving the disadvantages of the aforementioned prior art, the technical objective of the present invention is to provide a portable laser treatment device, which can cut off irradiation of a laser beam without manual manipulation by a surgeon if the surface to be irradiated is at a certain distance from the beam Moreover, another objective of the present invention is to provide a portable laser treatment device, which allows minimization its volume while having equal or superior cooling capacity as compared to that of the conventional portable laser treatment device.

In order to achieve the aforementioned technical objectives, in relation to a portable laser treatment device, which comprises a case; a semiconductor laser diode placed inside said case, which irradiates laser, a condensing lens installed at the front portion of said semiconductor laser diode; a power supply; a power switch installed outside said case, which controls supply of power; an irradiation switch, witch controls irradiation of laser, and a controller which controls the operation of said device according to the manipulation of said switch, the present invention comprises a distance-sensing sensor, installed to said case, for measuring the distance between the surface to be irradiated from the condensing lens; and said controller for receiving signals from said dance-sensing sensor, and then cutting off irradiation of laser if the distance between the tissue to be irradiated from the condensing lens is greater than the focal distance of the condensing lens.

For sensing distance, it is more advantageous to install said distance-sensing sensor at the upper portion where the condensing lens is installed. Even where the power switch or the irradiation switch is turned on, if the surface to be irradiated (i.e., the site of the body under treatment) is greater than the focal distance of the condensing lens, it is so designed to cut off irradiation of laser by means of a controller. By this process, the laser is not irradiated thereon no further than a certain distance.

Moreover, in relation to said portable laser treatment device, the present invention comprises a thermal electric cooler at the rear side of said semiconductor laser diode.

As described above, due to its characteristics, the semiconductor laser diode discharges a lot of heat and therefore needs an appropriate means of cooling. In the present invention, a thermal electric cooler was used for cooling therein. A thermal electric cooler is attached rear to the side, which irradiates laser.

In relation to said portable laser treatment device, the present invention comprises placing an assembly of two or more of semiconductor laser diodes and thermal electric coolers into the case at a certain interval on its circumference; and installing a reflector which reflects lasers irradiated from the respective laser diodes towards the condensing lens.

Since there is a limitation as to the energy level of irradiation with just one semiconductor laser diode, several semiconductor laser diodes can be used in conjunction when a higher energy level is required. For this purpose, a multiple of semiconductor laser diodes are aligned around the circumference of the condensing lens so that they are respectively at an equal distance from the condensing lens. Further, a reflector is installed adjacent to the semiconductor laser diode so that the irradiated laser can be reflected toward the condensing lens.

Moreover, in relation to said portable laser treatment device, the present invention comprises installing a sound generation device for generating different sounds at the time of operations of said power switch and the irradiation switch, respectively.

DETAILED DESCRIPTION OF THE PREFERRED EMBODIMENTS

Figure 1:
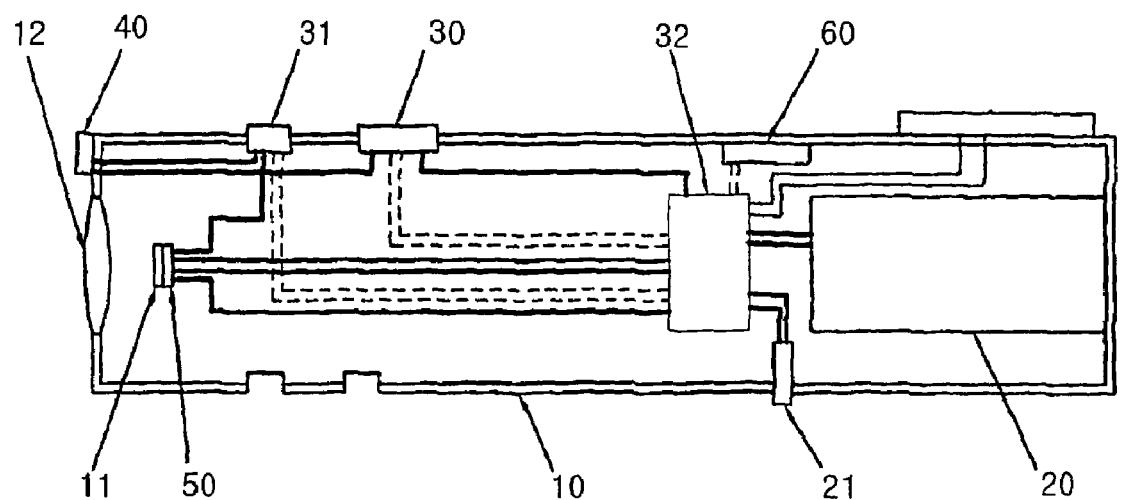
FIG. 1 is a lateral view, which illustrates one embodiment of the portable laser treatment device according to the present invention.

Below, the embodiments of the portable laser treatment device according to the present invention with references to the attached drawings are described in further detail. In FIG. 1, a case 10 has a hollow inside chamber of a cylindrical shape. In FIG. 1 at the end of the right side thereof there is a space for inserting a battery 20. At the lower side of the case 10, there is a terminal 21 for receiving outside power. The battery 20 and the power supply terminal 21 are connected to the controller 32 to supply power to the controller 32. At the upper side of the controller 32, there is a sound generation device 60 for outputting sounds pre-stored in the controller 32.

A condensing lens 12 is installed at the end of the left side of the case 10. On the top thereof there is a distance-sensing sensor 40. As for the distance-sensing sensor 40, an infrared sensor used generally can be utilized herein. On the ride side of the condensing lens 12, there is a semiconductor laser diode 11, as installed therein, and the laser diode 11 is attached to the rear side of the thermal electrical cooler 50.

A power switch 30 and an irradiation switch 31 are installed on the top of the left side of the case 10. By operating the power switch 30, power is supplied to the distance-sensing sensor 40, the controller 32, and the sound generation device 60, respectively. As such, the distance-sensing sensor 40 measures the distance between the surface to be irradiated from the condensing lens 12. The sound generation device 60 informs the user as to the operation status of the device by outputting different pre-set sounds.

Then, by turning on the irradiation switch 31, power is supplied to the thermal electrical cooler 50, and the semiconductor laser diode 11, respectively and then the laser is irradiated. Here, if the distance measured by the distance-sensing sensor 40 is greater than the focal distance of the condensing lens 12, the controller 32 detects this and cuts off irradiation of laser. Moreover, when the irradiation switch 31 is turned on, different sounds are outputted from said sound generation device 60, and it informs acoustically as to the fact that the laser is irradiating.

As illustrated in the drawings, it should be preferably designed to allow installation of a battery inside the case 10. In view of the power consumptions of the laser diode 11 and the thermal electric cooler 50, it may be impossible to operate the device for a long time by battery. However, in case of emergency such as a temporary power outage during surgery, it may be possible to continue operating without stopping by way of said battery.

Figure 2:
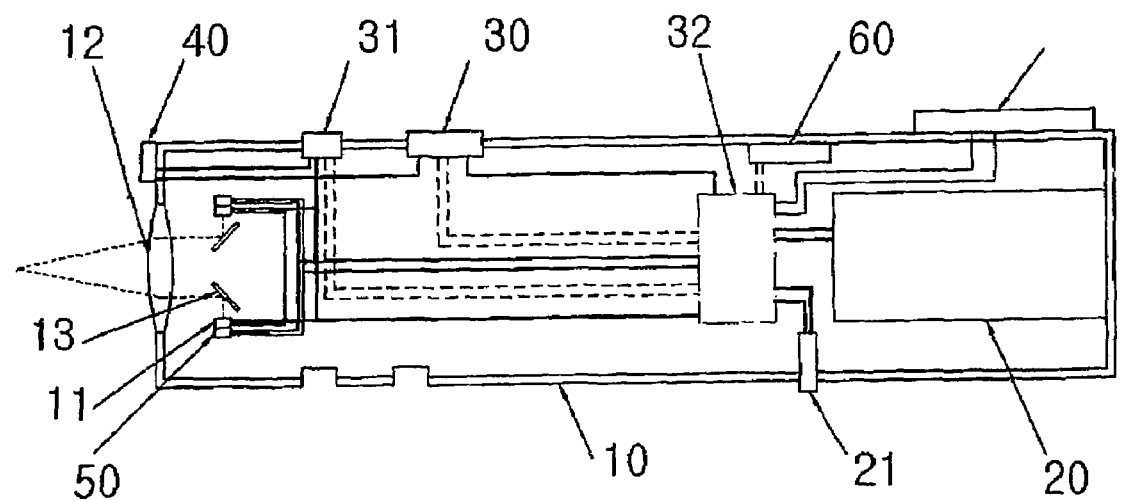
FIG. 2 is a lateral view, which illustrates another embodiment of the portable laser treatment device according to the present invention.

In FIG. 2, another embodiment of the portable laser device is illustrated. In the embodiment to raise the energy level of the irradiated laser, two semiconductor laser diodes 11 are used. To the rear side of the respective laser diodes 11, the thermal electric cooler 50 is attached thereto. Moreover, the semiconductor laser diode 11 is aligned around the circumference thereof at an equal interval. It is structured in such a way that the respective semiconductor laser diodes 11 are at an equal distance from the condensing lens 12 as a center.

A reflector 13 is installed therein, further in the radial direction than that of the semiconductor laser diode 11. The reflector 13 reflects the irradiated laser from the semiconductor laser diode 11 and causes irradiation of the laser in the direction of the condensing lens 12.

Figure 3:
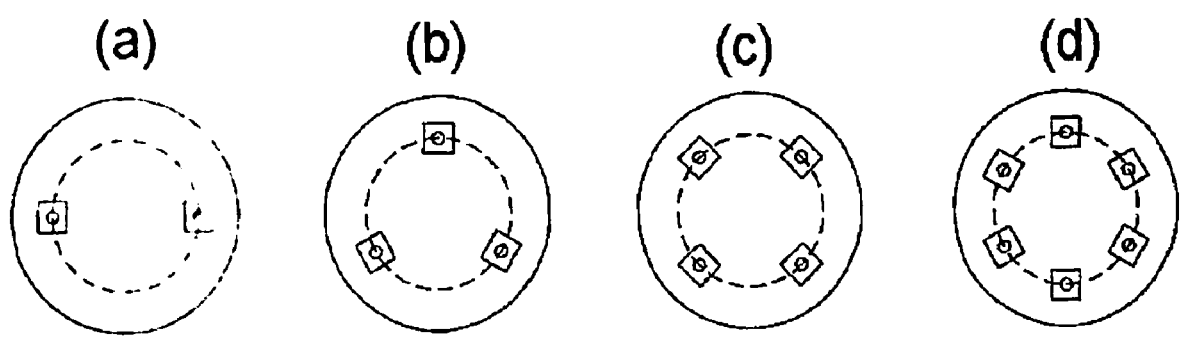
FIG. 3 is a layout drawing, which illustrates placements of a multiple of semiconductor laser diodes in the embodiment of FIG. 2.

Depending on the need of energy levels of the laser, it may be required to install more semiconductor laser diodes 11. In FIG. 3, the method of installing them is illustrated in case of using a multiple of semiconductor laser diodes 11.

INDUSTRIAL APPLICABILITY

According to the present invention having the aforementioned structure as such, it allows prevention of laser irradiation by means of a distance-sensing sensor when the surface to be irradiated is greater than a certain distance from the laser treatment device of the present invention. As such, it is possible to carry out safer operation from the perspectives of patents and surgeons alike by allowing the surgeons to concentrate solely on the surgeries by way of lessening the concerns for careless handling of the laser treatment devices.

Moreover, since the present invention uses a thermal electric cooler, it can further reduce the volume of the laser treatment device. Further, by installing a sound generation device, the operation status can be checked visibly and acoustically, and in the end, the present invention has the effect of facilitating its carriage and handling.

What is claimed is:

1. A portable laser treatment device, having a case (10); a semiconductor laser diode (11), placed inside said case (10), which irradiates laser, a condensing lens (12) installed at the front portion of said semiconductor laser diode (11); a power supply, a power switch (30), installed outside said case (10), which controls supply of power, an irradiation switch (31), which controls irradiation of laser; and a controller (32) which controls the operation of said device according to the manipulation of said switch, wherein said device comprises a distance-sensing sensor (40), installed into said case (10), for measuring the distance between a surface to be irradiated from the condensing lens (12); and said controller (32), for receiving signals from said distance-sensing sensor (40), which cuts off irradiation of laser if the distance between tissue to be irradiated from the condensing lens (12) is greater than the focal distance of said condensing lens (12).

2. The portable laser treatment device according to claim 1, which comprises a thermal electric cooler (50) at the rear side of said semiconductor laser diode (11).

3. The portable laser treatment device according to claim 2, which comprises placing an assembly of two or more of semiconductor laser diodes (11) and thermal electric coolers (50) into the case (10) on its circumference; and installing a reflector (13) which reflects lasers irradiated from the respective laser diodes (11) towards the condensing lens (12).

4. The portable laser treatment device according to one of claims 1, 2 or 3, which comprises installing a sound generation device (60) in the case (10) for generating different sounds at the time of operations of said power switch (30) and the irradiation switch (31), respectively.

* * * * *